Figure 1:
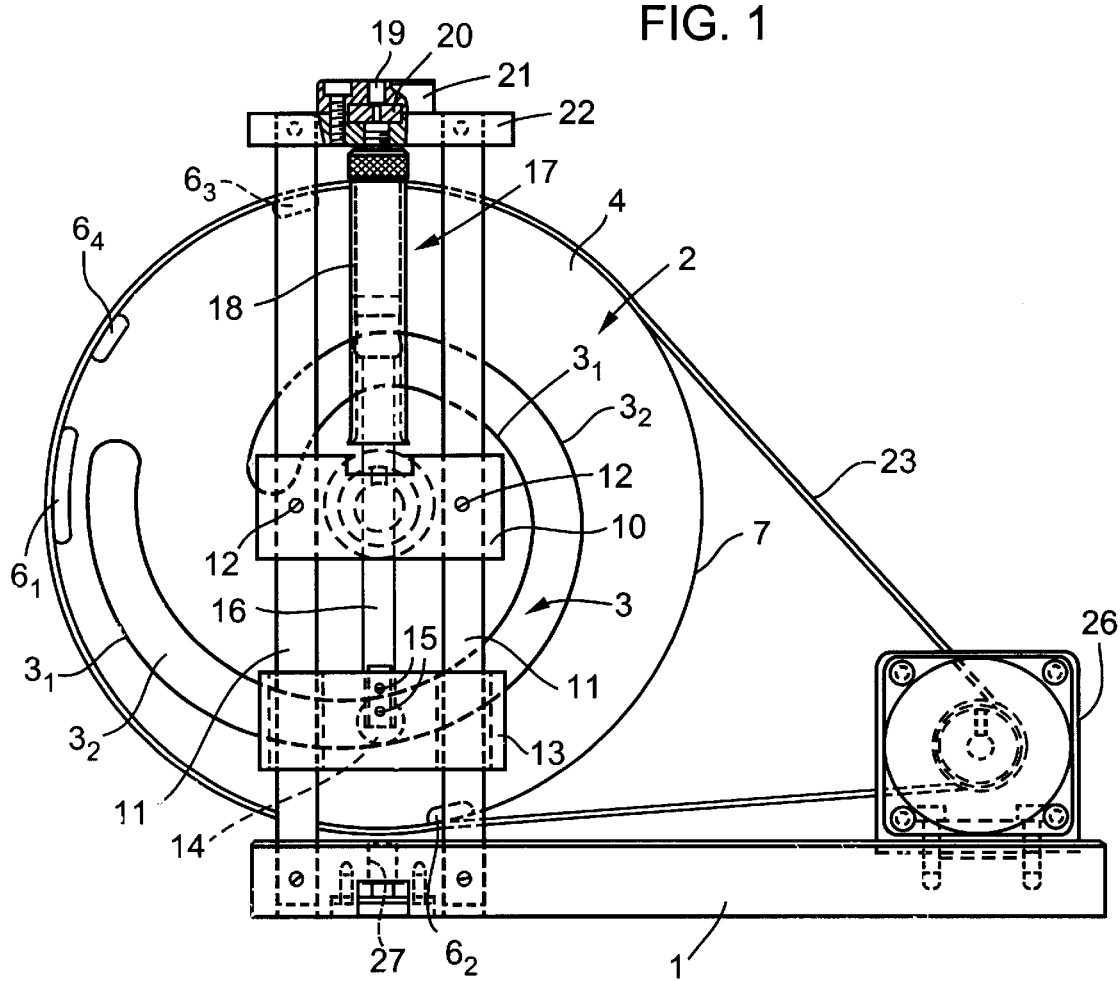
Figure 2:
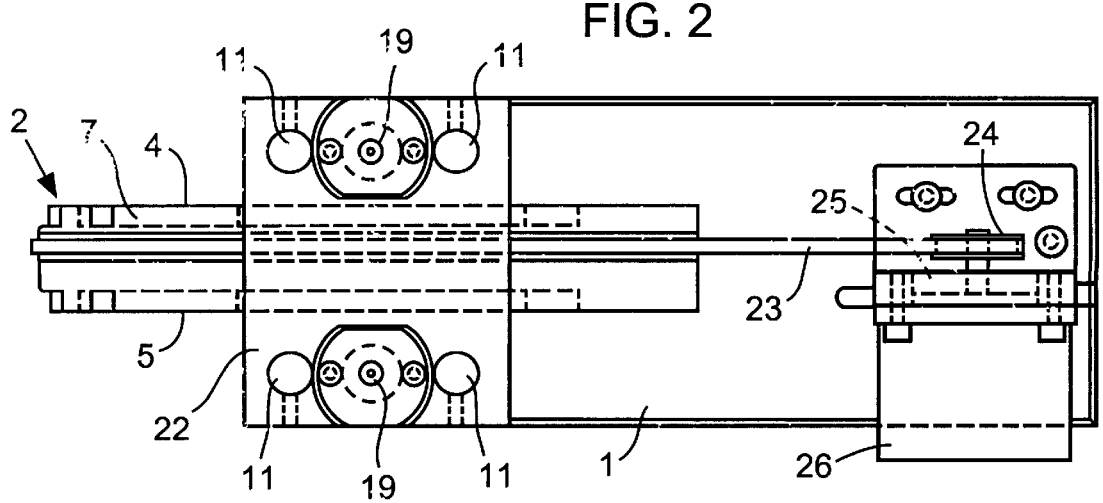
Figure 3:
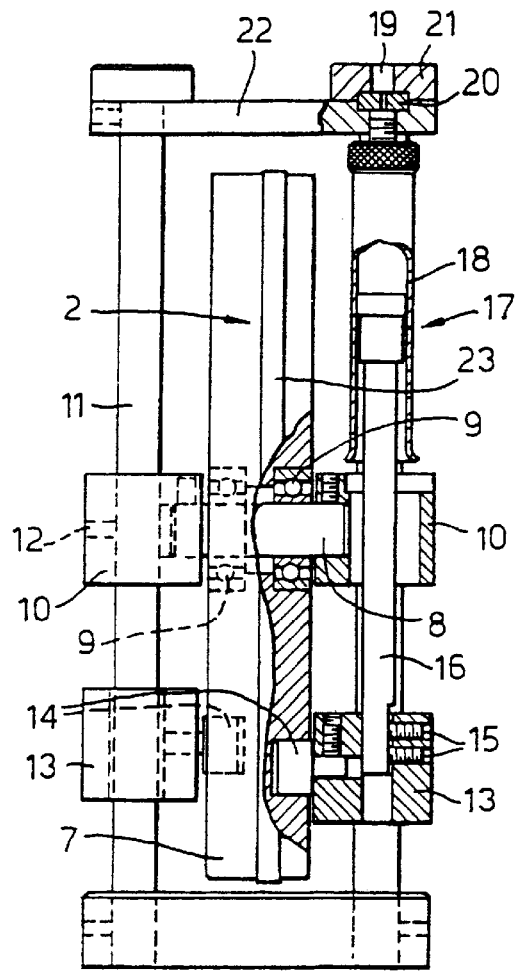

United States Patent
Shine et al.

[11] Patent Number: 6,070,476
[45] Date of Patent: Jun. 6, 2000

[54] FLUID DELIVERY METHOD

[76] Inventors: Thomas Adam Shine, 220 Lawrence St., No. 3 New Haven, Conn. 06511; Ian Basil Shine, 444 Central Park West, New York, N.Y. 10025

[21] Appl. No.: 09/101,012
[22] PCT Filed: Dec. 27, 1996
[86] PCT No.: PCT/GB96/03258
    § 371 Date: Aug. 4, 1998
    § 102(e) Date: Aug. 4, 1998
[87] PCT Pub. No.: WO97/24529
    PCT Pub. Date: Jul. 10, 1997

[30] Foreign Application Priority Data

Dec. 29, 1995 [GB] United Kingdom .................. 9526653

[51] Int. Cl.[7] ............................................... G01N 1/00
[52] U.S. Cl. .............................................. 73/864.81
[58] Field of Search .......................... 73/863.31–863.33, 73/864.81, 864.17, 864.13, 864.16, 864.21, 864.22; 222/135, 136, 137, 280, 145.1

[56] References Cited

U.S. PATENT DOCUMENTS

| 3,726,144 | 4/1973 | Klein . |
| 3,902,852 | 9/1975 | Lemieux et al. . |
| 5,540,498 | 7/1996 | Chu . |

FOREIGN PATENT DOCUMENTS

| 0 334 994 | 10/1989 | European Pat. Off. . |
| 2 096 275 | 2/1972 | France . |
| 2 068 544 | 8/1981 | United Kingdom . |
| 87 03092 | 5/1987 | WIPO . |
| 94 02945 | 3/1994 | WIPO . |

*Primary Examiner*—Robert Raevis
*Attorney, Agent, or Firm*—Burns, Doane, Swecker & Mathis, L.L.P.

[57] ABSTRACT

A fluid delivery apparatus comprising two or more delivery syringes (17), each delivery syringe comprising a syringe housing (18) defining a tube with a passage having a fluid outlet, and a syringe plunger arranged to slide axially within the tubular passage and seal one end of the tubular passage. The apparatus also includes a syringe plunger drive arranged to drive the syringe plunger along at least part of the length of the tubular passage according to a predetermined velocity profile or the delivery syringe and discharge fluid through the fluid outlet. The predetermined velocity profile of each delivery syringe is such that, in use, a combined flow rate fluid discharge simultaneously from the outlets from the delivery syringes is maintained substantially constant over at least a quarter of the range of movement of each of the plungers. In a preferred example, the syringe plunger drive comprises a rotatable cam (2) and a cam follower (14), being coupled to the syringe plunger to drive the syringe plunger as the cam is rotated.

12 Claims, 3 Drawing Sheets

FLUID DELIVERY METHOD

TECHNICAL FIELD

The present invention relates to an apparatus which is capable of providing any desired ratio of two or more fluids or suspensions and whose relative concentrations may be varied accurately.

BACKGROUND ART

GB-B-2,068,544, discloses a method and apparatus in which the properties of a dilute sample of red blood cells are changed by osmosis to generate a set of related data which is characteristic of the health or physiological condition of the human or animal source of the blood cell sample. By subjecting cells to a number of solutions having different concentrations, the size and shape of the blood cells changes. When these changes are measured electronically, a detected electrical resistance increases to a peak and then falls as the critical concentration passes.

In particular, in GB-B-2,068,544 it is known to be desirable to obtain a series of hypotonic concentrations and thereby measure the characterisetics of blood cells at a series of different osmalolities. In the past, a conventional stepper motor has been used in combination with a lead-screw apparatus to drive a plunger of a first syringe containing a dilutent which is subsequently mixed with a different dilutent contained in a second syringe, the plunger of which is driven by a second stepper motor. A third syringe containing a prepared blood cell sample is discharged at a constant rate into a mixing chamber into which the first and second syringes simultaneously discharge their contents. During the test, the flow rate of fluid from the first syringe is typically decreased over a period of time whilst the flow rate of fluid from the second syringe is correspondingly increased over the same period to change the relative concentrations of the two dilutents whilst size, shape and count measurements are made of the blood cells in the resulting mixture. However, conventional stepper motors can only be driven at a limited number of predetermined stepping rates so that the velocity of fluid discharged from each syringe can only be changed in a stepwise manner, which therefore only very roughly approximates to a desired velocity profile. Each stepwise change in velocity of the conventional stepper motor leads to disturbances in the flow of fluid which affects the accuracy of the size, shape and count measurements made downstream. Accordingly, the accuracy of this conventional arrangement for determining cell osmolality is only to within 2–3 mosm $Kg^{-1}$, which is not sufficiently sensitive to detect certain health or physiological conditions.

DISCLOSURE OF INVENTION

According to a first aspect of the present invention, a fluid delivery method and apparatus comprises first and second delivery syringes, each delivery syringe comprising a syringe housing defining a tubular passage having a fluid outlet, and a syringe plunger arranged to slide axially within the tubular passage and seal one end of the tubular passage, the fluid delivery apparatus further comprising syringe plunger drive means for driving the syringe plunger of the first and second syringe along at least part of the length of the tubular passage according to a predetermined velocity profile for the delivery syringe and discharge fluid through the fluid outlet, wherein the predetermined velocity profile of each delivery syringe is such that, in use, a combined flow rate of fluid discharged simultaneously from the outlets of the plurality of delivery syringes is maintained substantially constant over at least a portion of the range of movement of the plurality of plungers.

In the present invention, means are provided to drive the plunger of each delivery syringe in a substantially continuous manner according to a desired velocity profile, a portion of which profile results in an acceleration in the rate of discharge of fluid. This profile may be any continuous function, whether linear or otherwise. The predetermined velocity profile for each syringe determines the rate at which fluid is discharged from the syringe over a range of movement of the syringe plunger. In an apparatus for measuring cell properties the fluid outlet of each delivery syringe is connected to a remote mixing and sensing chamber upstream of the apparatus for taking size, count and other measurements. When used in such an apparatus, the fluid delivery apparatus of the present invention ensures that the combined flow rate of fluid remains substantially constant for at least the period that test measurements are being made even though the relative concentration of dilutents may be changing continuously.

Our co-pending British Patent application No. 9526717.5 also filed this day, describes a digital frequency generator which can be used to control a stepper motor in a conventional lead-screw fluid delivery arrangement. This frequency generator allows the stepping rate of the stepper motor to be set accurately and with minimal delay at a vastly increased number of discrete values so that the acceleration of the syringe plunger, and hence the flow rate of fluid discharged from the syringe, can be accelerated in a manner corresponding to a substantially continuous profile rather than a step function. Accordingly, this arrangement constitutes one embodiment of the present invention.

In the preferred embodiment of the present application, the syringe plunger drive means comprises a rotatable cam and a cam follower, the cam follower being coupled to the syringe plunger to drive the syringe plunger as the cam is rotated.

Preferably, the cam comprises a plate having a boxed profile formed in one face of the plate. Preferably, the cam follower is of roller type which is arranged to sit within the boxed profile. The boxed profile is formed in accordance with the predetermined velocity profile associated with the delivery syringe and required test routine. The cam plate may be formed from a plastics material, but preferably is formed from a metal. More preferably, the cam plate is formed from anodized aluminium.

The boxed profile eliminates the need for a spring return mechanism such as those found in car engines. By eliminating the springs, the torque required to drive the cam is reduced and the positional accuracy is improved because the resisting torque is always constant.

The boxed profile may be continuous so that the cam follower always returns to its original position after one complete revolution of the cam plate. However, this would mean that the cam would have to have a relatively large diameter, using more material, making the cam heavier and more costly, and therefore preferably, the cam is of a reciprocating type. In this case, the cam follower is returned to its original position by reversing the direction of rotation of the cam.

Preferably, the boxed profile is such that when the cam is rotated in one direction the cam follower bears against one side face of the box profile and when rotated in the opposite direction the cam follower bears against an opposite side face of the box. Preferably, the opposite side faces of the box are provided with different profiles. In this manner, the cam follower can drive the syringe plunger according to the predetermined velocity profile when rotated in the first direction to discharge fluid from the delivery syringe and when the cam is rotated in the opposite direction the cam follower can drive the syringe plunger according to another predetermined function to return the syringe plunger to its original position. Preferably, fluid is drawn into the delivery syringe from a source during the return stroke of the cam.

Preferably, the cam plate is rotatably supported at its centre on a fixed horizontal shaft, whereby the cam plate rotates about the fixed shaft on bearings.

Preferably, the cam follower is coupled to a drive block which in turn is coupled to the syringe plunger. Preferably, the drive block is free to slide vertically along a pair of supporting guide shaft.

Most preferably, a second boxed profile defining a second predetermined velocity profile is formed in the opposite face of the cam plate and a second cam follower, also coupled to its own drive block and pair of guide shafts, is arranged to drive a syringe plunger of a second delivery syringe. Accordingly, as the cam plate is rotated, two delivery syringes can be discharged simultaneously, each being discharged according to the predetermined velocity profile associated with its respective boxed cam profile. The advantage of this arrangement is that the first and second boxed cam profiles may be aligned to each other to within minutes of seconds of degrees i.e. to the limit of the CNC machine used to cut the cam plate, so that there is never any need to make fine manual timing adjustments as the two boxed cam profiles can never move over the life of the instrument, even if dropped or jarred.

Preferably, the fixed shaft supporting the cam plate is supported at each of its opposite ends by a support block which is itself supported on an adjacent pair of guide shafts. More preferably, the support blocks are releasable so they are capable of sliding along their respective guide shafts to adjust the height of the cam plate. The fixed shaft reduces the width of the apparatus and allows the delivery syringes to be mounted very close to the cam followers, thereby reducing the moment distance.

Preferably, the cam plate is circular and rotated by means of a drive belt which runs around the cam edge. More preferably, the drive belt is toothed and the cam edge is knurled. This has the advantage of driving the cam plate directly with a minimum number of mechanical links, substantially zero backlash and maximum torque.

Preferably, the drive belt is connected to a constant speed motor. Suitable motors include stepper, DC or geared motors. The motor drives the cam plate at a constant speed when discharging fluid from the delivery syringes.

Preferably, the cam edge of the cam plate is provided with a number of timing notches formed at the same time as the cam plate is manufactured which are detected by an optical sensor to determine the position of the cam. Preferably, the timing notches indicate top dead centre, bottom dead centre, and start and end positions for a range of cam movement which is of analytical interest. During assembly, the height of the cam plate is adjusted by sliding the fixed shaft and support blocks along their respective guide shafts to adjust the focal depth of the optical sensor. Once cut, the timing notches need never be adjusted.

According to a second aspect of the present invention, in a method of testing cell properties using the apparatus according to the first aspect of the present invention, a cellular sample contained in a first delivery syringe is discharged and mixed with dilutents discharged from a number of other delivery syringes.

In one method, the cellular sample is contained in a first delivery syringe and is discharged at a constant rate. The cellular sample is subsequently mixed with dilutents from two or more delivery syringes which are discharged at a variable rate for at least a portion of the test, wherein the combined flow of fluid discharged from all the delivery syringes remains substantially constant.

In a preferred method, only two delivery syringes are used. In this case, the cellular sample is premixed with a first dilutent to form a fluid source which supplies a first delivery syringe and a second dilutent forms another fluid source which supplies a second delivery syringe. This removes the need for a third delivery syringe. As the induced cell size changes when using the apparatus of the first aspect can be so small over only a small change in concentration gradient, measurement errors can be potentially serious. Pre-mixing improves the quality of test data as the cells of the sample are substantially uniformly distributed. In contrast, in three syringe systems, small concentrated pockets of sample cells can form which leads to significant measurement errors.

BRIEF DESCRIPTIONS OF DRAWINGS

An example of a fluid delivery apparatus in accordance with the present invention will now be described in detail with reference to the accompanying drawings, in which:

FIG. 1 shows a front view of a fluid delivery apparatus;

FIG. 2 shows a plan view of the fluid delivery apparatus;

FIG. 3 shows a partially exposed and sectioned end view of the fluid delivery apparatus;

FIG. 4 shows a cross-sectional view of a delivery syringe connector;

FIG. 5 shows a pair of velocity profiles for fluid discharged from two delivery syringes; and, FIG. 6 shows a pair of displacement profiles for syringe plunders of the delivery syringes.

DETAILED DESCRIPTION

In FIGS. 1 to 3, the fluid delivery apparatus comprises a base plate 1, an anodized aluminium cam disc 2 having a first boxed cam profile 3 cut in one face 4 and a second boxed cam profile (not shown) cut in an opposite face 5. In this example, the profiles of opposite faces $\mathbf{3}_1$, $\mathbf{3}_2$ of the boxed cam profile 3 are shown as identical, although it is possible to form one face $\mathbf{3}_1$ with a first continuous profile and face $\mathbf{3}_2$ with another continuous profile, for reasons described in detail below.

The cam disc 2 has a number of timing notches $\mathbf{6}_1$–$\mathbf{6}_4$, which are cut at the cam edge 7 on the one face 4 of the cam disc 2.

The cam disc 2 is supported on a fixed shaft 8 with bearing assemblies 9 located within the cam disc 2. The shaft 8 is supported at its two ends in support blocks 10 which are each supported by a pair of guide shafts 11 and held in place by grub screws 12. The height of the support blocks 10, and thus the cam disc 2, is adjustable by sliding the support blocks 10 up or down on the guide shafts 11.

A sliding block 13 is also mounted on each of the guide shafts 11 and coupled to a respective low friction steel roller cam follower 14. The roller cam follower 14 comprises a miniature shaft bearing with a central shaft extending into the sliding block 13. As shown in FIG. 1, the cam follower 14 sits within the boxed cam profile 3 formed in the face 4 of the cam disc 2 and is free to roll along the face of the boxed cam profile. Furthermore, the sliding block 13 is fixed to one end of a syringe plunger 16 with two set screws 15 associated with a vertically mounted delivery syringe 17. An upper end of the delivery syringe housing 18 is provided with a fluid inlet/outlet 19, which includes an inert PTFE washer 20. The PTFE washer 20 ensures fluid passing through the fluid inlet/outlet 19 flows into a PTFE delivery tube (not shown) without touching any other material. The PTFE washer 20 is held in place by a retaining clamp 21 which receives an open end of the PTFE tube (not shown).

The upper end of each delivery syringe housing 18 is screwed into a top plate 22 which also serves to brace the two opposite pairs of guide shafts 11.

The cam disc 2 is arranged to be driven about its flat cam edge 7 by a toothed power transmission belt 23 which is coupled to a pulley 24 of a stepper motor 25. The stepper motor 25 is secured to the base plate 1 on an L-shaped bracket 26. The apparatus also comprises a pair of spaced apart optical sensors (not shown) which are mounted in a socket 27 in the base plate 1 immediately below the cam disc 2. These optical sensors detect the timing notches $6_1$–$6_4$ as the cam disc 2 is rotated.

In operation, the stepper motor 25 drives the cam disc 2 anti-clockwise (with respect to the view shown in FIG. 1) to refill each of the delivery syringes 17 with fluid from two separate sources (not shown). As the cam disc 2 rotates, the cam follower 14 located inside the boxed cam profile 3 is pushed downwards, which pushes down on the sliding block 13 to which the syringe plunger 16 is attached. The sliding block 13 is guided vertically by the same guide shafts 11 which support the cam shaft 8 and support blocks 10. The two reflective optical sensors, typically elements from pen-sized bar codes readers located beneath the cam disc 2 in the mounting socket 27, determine the position of the cam disc by detecting the timing notches $6_1$–$6_4$ cut into the edge 7 of the cam disc 2. The timing notches $6_1$–$6_4$ identify, respectively, top dead centre, two transitions which mark a region of particular analytical interest when making test measurements, and bottom dead centre.

Once the optical sensors (not shown) detect that the cam disc 2 is at bottom dead centre $6_4$ i.e. when each of the delivery syringes 17 has been refilled, the stepper motor 25 is stopped, reversed and started again. The stepper motor 25 turns the cam disc 2 at a constant speed which forces the delivery syringes 17 to discharge fluid in accordance with the velocity profiles associated, respectively, with the boxed cam profiles cut into the cam disc 2.

Figure 4:
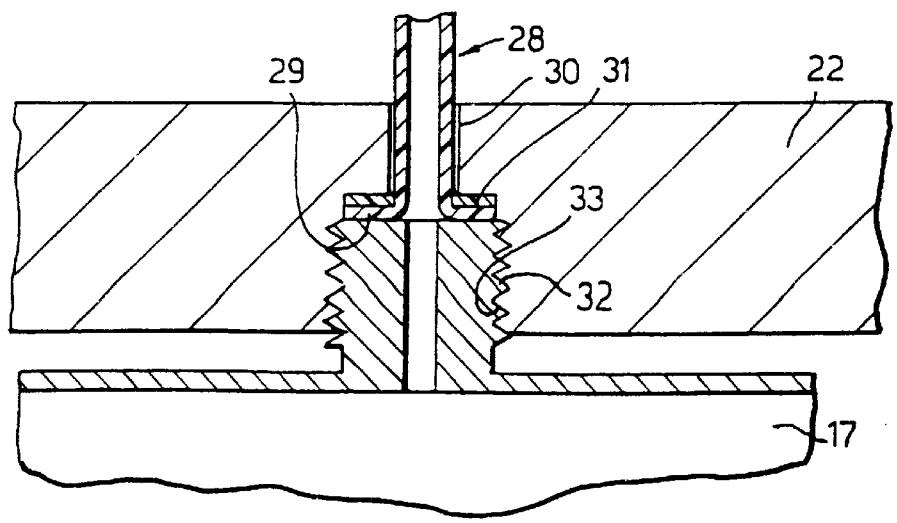

FIG. 4 shows a cross-sectional view to illustrate another arrangement for connecting the delivery syringe 17 to a PTFE tube 28.

In the arrangement, a pre-flared end 29 of the PTFE tubing 28 is inserted through a slot 30 formed in the front of the plate 22 and through a PTFE washer 31. Conventionally, the tubing 28 would be threaded through an aperture and flared in situ. Accordingly, this arrangement is much more simple and allows the use of commercially available pre-flared tubing. The inlet/outlet of the delivery syringe 17 includes a screw threaded portion 32 which is screwed into a correspondingly threaded portion 33 formed in the top plate 22. When the delivery syringe is fully screwed in, the top of the delivery syringe 17 engages the bottom of the flared portion 29 of the PTFE tube 28 to seal the top of the syringe.

As described above, it is possible to form one face $3_1$ of the boxed cam profile 3 with a first continuous profile and the other face $3_2$ with another continuous profile. In this manner, the cam follower 14 can drive the syringe plunger 16 according to the predetermined velocity profile when rotated anti-clockwise and bearing against the first face $3_1$ and when the cam plate 2 is rotated in the opposite direction, the cam follower 14 can drive the syringe plunger 16 according to another predetermined function associated with the face $3_2$ to return the syringe plunger 16 to its original position.

Figure 5:
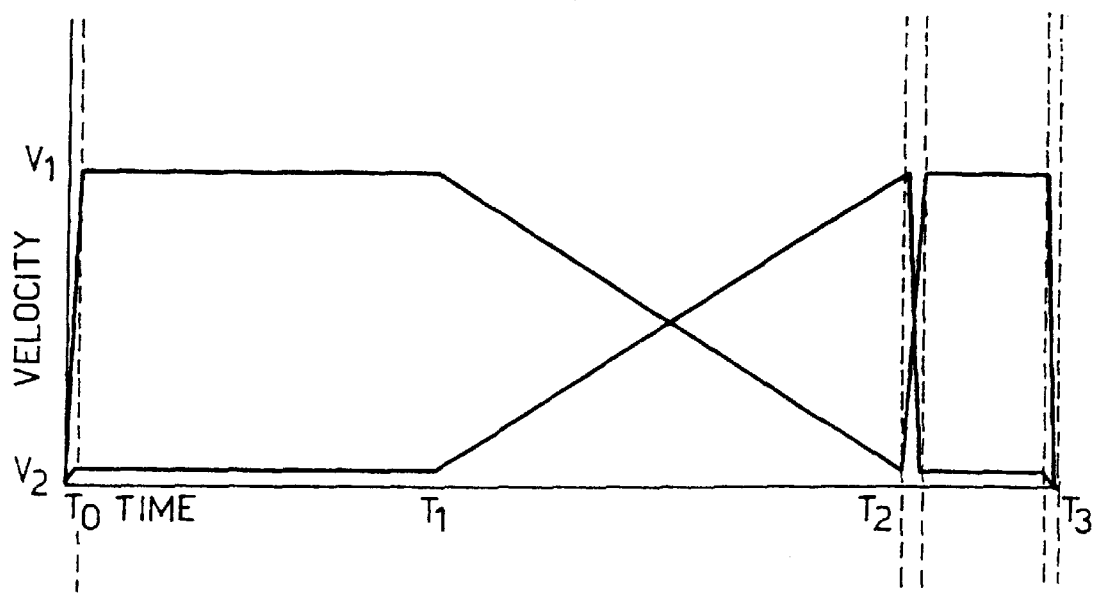
Figure 6:
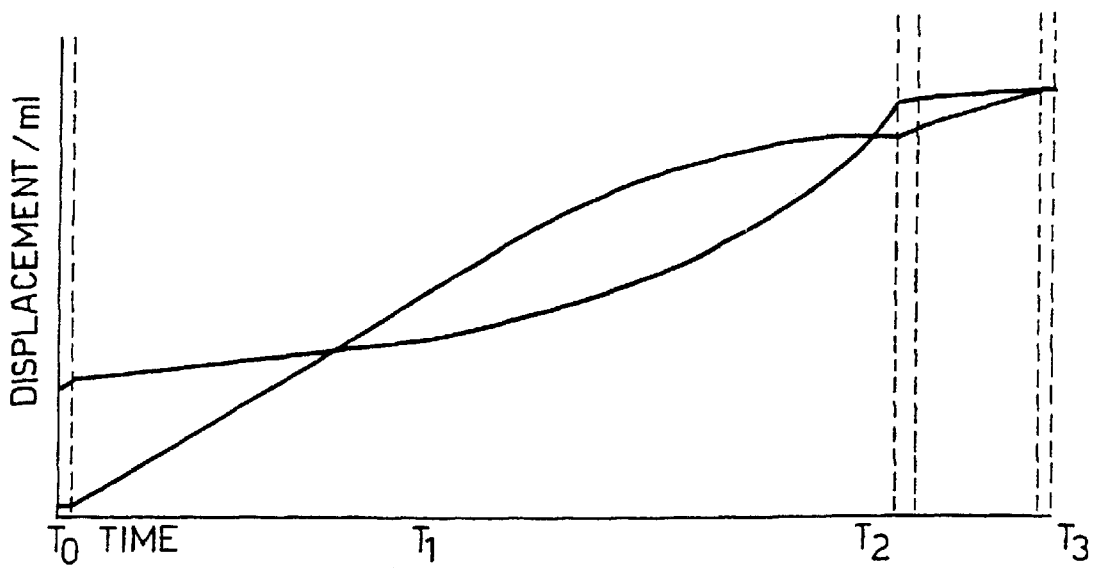

FIGS. 5 and 6 show, respectively, graphs of velocity against time for fluid discharge from the two delivery syringes 17 and the relative displacement of the syringe plungers 16 of the two delivery syringes 17.

In this example, a first dilutent, such as a saline sample, is mixed with a second dilutent, such as a sample of pure water. As shown in FIG. 5, the cam profile associated with the delivery syringe filled with the first dilutent accelerates the syringe plunger to discharge fluid at a velocity $V_1$, whilst the cam profile associated with the other delivery syringe 17 filled with the second dilutent accelerates the syringe plunger to discharge fluid at a lower velocity $V_2$.

Once a constant flow rate from each delivery syringe 17 has been established at time $T_0$, at time $T_1$, as determined by timing notch $6_2$, the cam profile associated with the delivery syringe filled with the first dilutent causes the rate of fluid discharge to decelerate linearly over the period $T_2$–$T_1$, where $T_2$ is indicated by the timing notch $6_3$, to a velocity $V_2$, while simultaneously, the cam profile associated with the delivery syringe filled with the second dilutent causes the rate of fluid discharge to accelerate linearly to velocity $V_1$. During this period, the combined flow rate of the two syringes remains substantially constant. Finally, the two syringes are emptied over the period $T_3$–$T_2$, until the syringe plunger reaches top dead centre, as indicated by timing notch $6_4$.

During the test, it is important that the velocities $V_1$ and $V_2$ do not approach zero. This is to ensure that no fluid from one delivery syringe enters the other or has the chance of entering the other's PTFE outlet tube.

In a test method for measuring cell properties, a cell sample is pre-mixed with a dilutent, usually a physiological buffer such as saline, before the dilutent is drawn into a delivery syringe 17. This pre-mixing improves the quality of the test data as the cells are distributed uniformly within the mixture when it is discharged into a mixing chamber (not shown) above together with a second dilutent loaded into the other delivery syringe 17. The apparatus typically produces a 200 $\mu$liter s$^{-1}$ combined output and is potentially accurate to within 0.1 mosm Kg$^{-1}$.

What is claimed is:

1. A method of testing cell properties of a cellular sample using a fluid delivery apparatus comprising at least first and second delivery syringes, each delivery syringe comprising a syringe housing defining a tubular passage having a fluid outlet, and a syringe plunger arranged to slide axially within the tubular passage and seal one end of the tubular passage, the fluid delivery apparatus further comprising syringe plunger drive means for driving the syringe plunger of the first and second syringe along at least part of the length of the respective tubular passage according to a predetermined velocity profile for the delivery syringe and discharging fluid through the fluid outlet, the method comprising the steps of:

a) premixing the cellular sample with a first dilutent to form a fluid source and supplying the first delivery syringe with the fluid source;

b) supplying the second delivery syringe with another fluid source; and c) sliding the plungers within the syringes with the drive means according to the predetermined velocity profile of each delivery syringe so that a combined flow rate of fluid discharged simultaneously from the outlets of the delivery syringes is maintained substantially constant over at least a portion of the range of movement of the plurality of plungers.

2. The method according to claim 1, in which the syringe plunger drive means comprises a rotatable cam and a cam follower, the cam follower being coupled to one of the syringe plungers to drive the syringe plunger as the cam is rotated.

3. The method according to claim 2, in which the cam comprises a plate having a boxed profile formed in one face of the plate, the profile being formed in accordance with the predetermined velocity profile associated with the first delivery syringe.

4. The method according to claim 3, in which the cam follower is of a roller type which is arranged to sit within the boxed profile.

5. The method according to claim 2, in which the cam is of a reciprocating type.

6. The method according to claim 3, in which the boxed profile is arranged so that when the cam is rotated in one direction the cam follower bears against one side face of the boxed profile and when rotated in the opposite direction the cam follower bears against an opposite side face of the box, wherein the opposite side faces of the box are provided with different profiles.

7. The method according to claim 2, in which the cam plate is rotatably supported at its center on a fixed horizontal shaft, whereby the cam plate rotates about the fixed shaft on bearings.

8. The method according to claim 2, in which the cam follower is coupled to a drive block which is in turn coupled to the syringe plunger, the drive block being free to slide vertically along a pair of supporting guide shafts.

9. The method according to claim 3, in which a second boxed profile defining a second predetermined velocity profile is formed in the opposite face of the cam plate and a second cam follower, also coupled to its own drive block and pair of guide shafts, is arranged to drive the syringe plunger of the second delivery syringe.

10. The method according to claim 2, in which the cam plate is circular and rotated by a drive belt around the cam edge.

11. The method according to claim 10, in which the drive belt is connected to a constant speed motor.

12. The method according to claim 2, in which the cam plate is provided with a number of timing notches which are capable of being detected by an optical sensor.

* * * * *